United States Patent [19]

Chin

[11] Patent Number: 4,696,304

[45] Date of Patent: Sep. 29, 1987

[54] THERMODILUTION FLOW-DIRECTED CATHETER ASSEMBLY AND METHOD

[75] Inventor: Albert K. Chin, Irving, Tex.

[73] Assignee: Thomas J. Fogarty, Palo Alto, Calif.

[21] Appl. No.: 855,143

[22] Filed: Apr. 23, 1986

Related U.S. Application Data

[63] Continuation of Ser. No. 648,822, Sep. 10, 1984, abandoned.

[51] Int. Cl.$^4$ ............................................. A61B 5/02
[52] U.S. Cl. .................................... 128/673; 128/692; 604/97; 604/159; 604/280
[58] Field of Search ................. 128/4, 325, 344, 348.1, 128/656–658, 668–670, 672–673, 675, 692, 772; 604/43, 45, 52–53, 96–97, 99, 159, 164, 280

[56] References Cited

U.S. PATENT DOCUMENTS

| | | | |
|---|---|---|---|
| 3,394,705 | 7/1968 | Abramson | 604/96 |
| 4,196,731 | 4/1980 | Laurin et al. | |
| 4,202,346 | 5/1980 | Granier | |
| 4,230,109 | 10/1980 | Geiss | 604/280 |
| 4,323,071 | 4/1982 | Simpson et al. | |
| 4,327,723 | 5/1982 | Frankhouser | |
| 4,333,254 | 6/1982 | Lundquist | 604/99 |
| 4,353,369 | 10/1982 | Mugherties et al. | 604/53 |
| 4,446,867 | 5/1984 | Leveen et al. | 128/344 |
| 4,502,488 | 3/1983 | Degironimo et al. | |
| 4,508,103 | 4/1985 | Calisi | 128/673 |

*Primary Examiner*—William E. Kamm
*Attorney, Agent, or Firm*—Limbach, Limbach & Sutton

[57] ABSTRACT

A catheter assembly for measuring hemodynamic pressure and method. The assembly includes an outer catheter and an inner catheter slidably mounted within the outer catheter lumen. The inner catheter is provided with an inflatable balloon which is used to guide the distal section of the assembly through the heart and to occlude a pulmonary artery or capillary. The inner catheter is provided with a lumen for inflating the baloon and a separate lumen for measuring pressure. The catheter assembly is inserted in the heart of the patient in the conventional manner. The inner catheter is advanced through the outer catheter until the inflated balloon occludes an artery or capillary. Once a pressure measurement is made through the separate inner catheter lumen, the inner catheter is retracted through the outer catheter and the balloon deflated. Subsequent pressure measurements may be made by simply reinflating the balloon and advancing the inner catheter through the fixed outer catheter.

19 Claims, 8 Drawing Figures

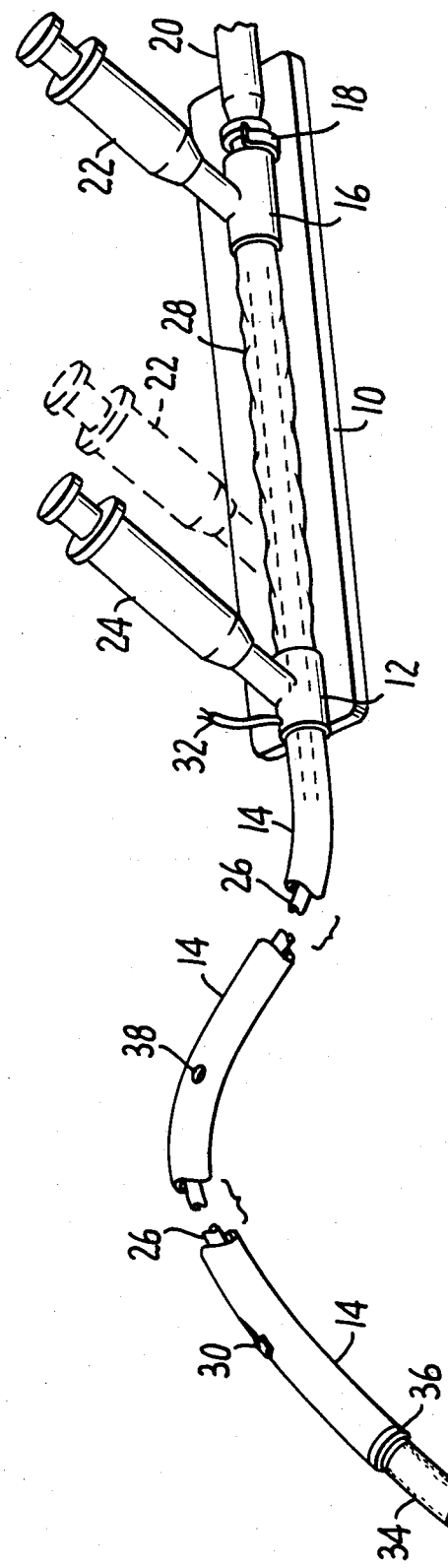
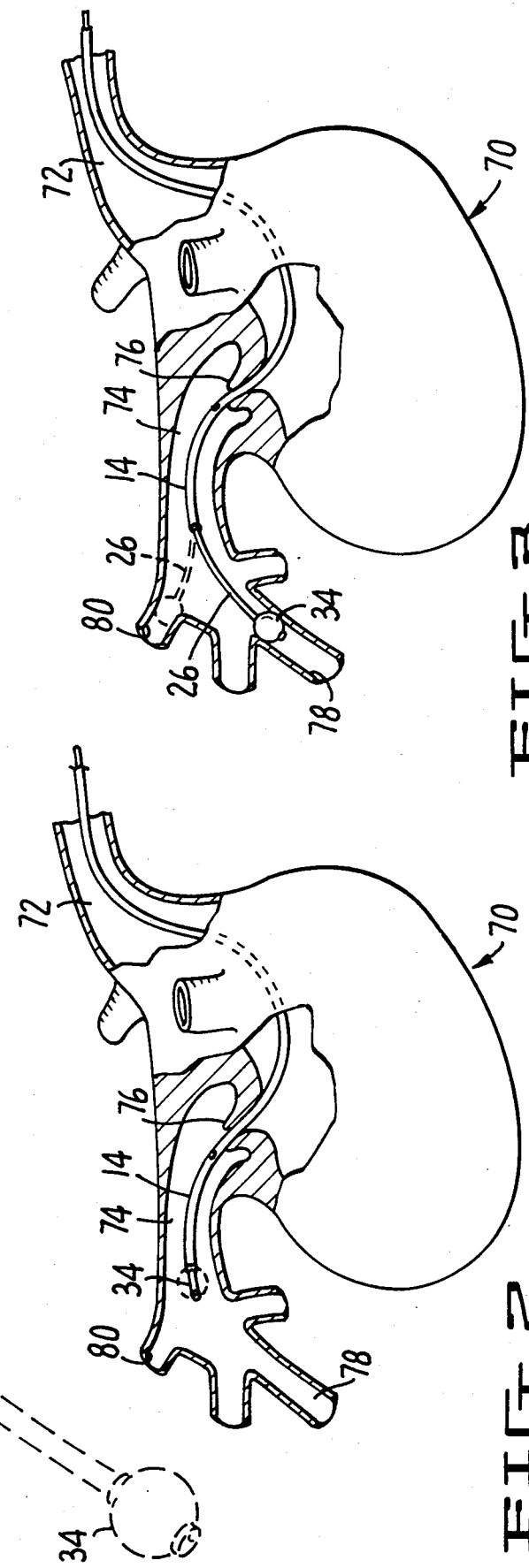
FIG. 1.
FIG. 2.
FIG. 3.

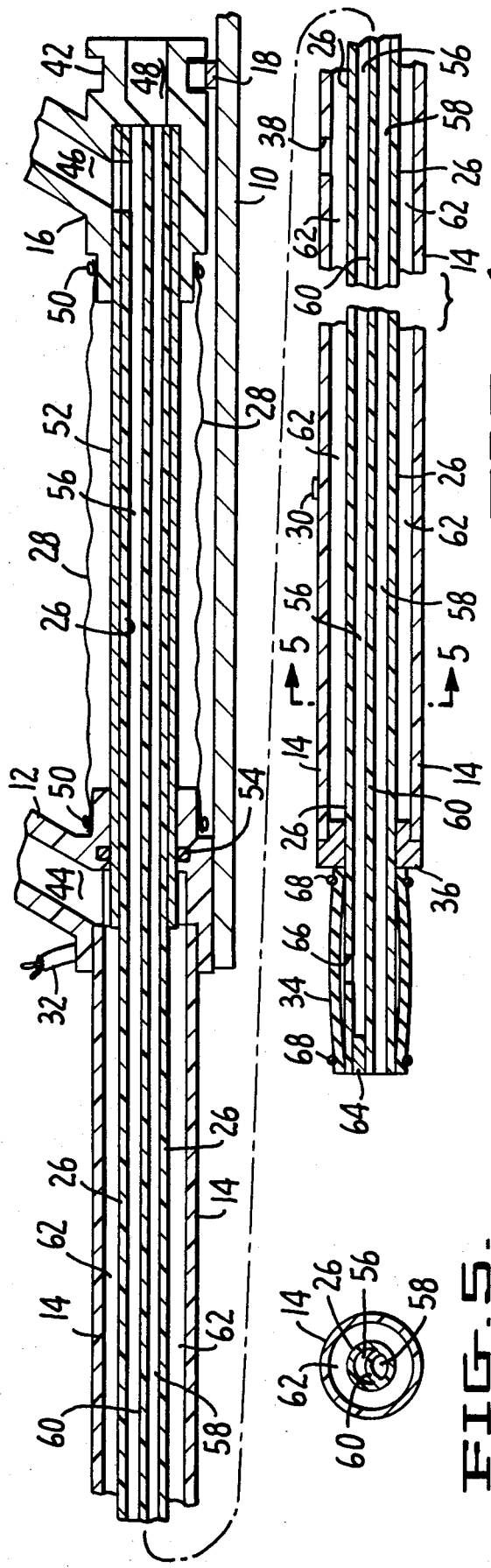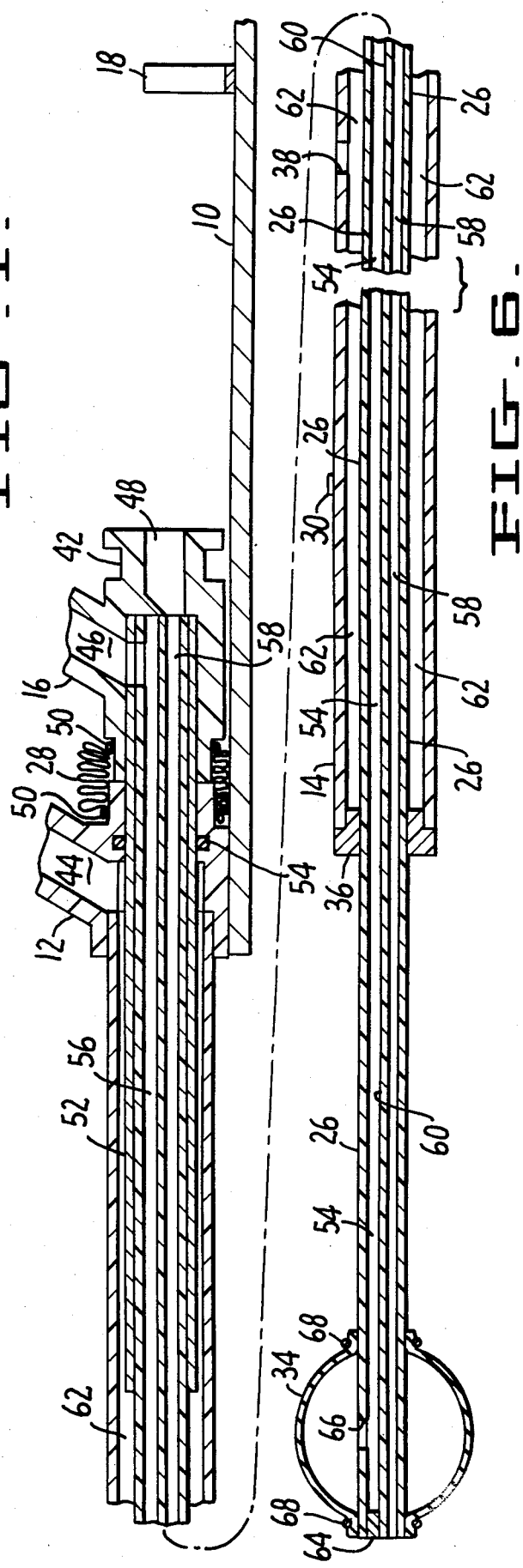

THERMODILUTION FLOW-DIRECTED CATHETER ASSEMBLY AND METHOD

This is a continuation of application Ser. No. 648,822, filed Sept. 10, 1984, now abandoned.

BACKGROUND OF THE INVENTION

1. Field of the Invention

The subject invention relates generally to catheters and, more particularly, to a thermodilution catheter assembly for cardiac monitoring and method.

2. Background Art

Catheters are commonly used in cardiac monitoring. One such catheter, sometimes referred to as a flow-directed thermodilution catheter, is used as a diagnostic tool for obtaining hemodynamic pressures of the heart. In addition, such catheters are frequently used for measuring cardiac output. The catheter is provided with three lumens, including a first lumen for inflating a balloon located at the distal catheter tip. A second lumen is included which is open at the distal catheter tip and which is used for measuring pressure. The third lumen extends along the length of the catheter and terminates typically 30 cm from the distal catheter tip. The catheter further includes a thermistor which is positioned between the distal tip of the catheter and the third lumen opening.

In operation, the catheter is introduced into a central vein and advanced toward the right heart through the superior vena cava. When the distal tip of the catheter is positioned within the vena cava, a small balloon located at the tip is inflated through the inflation lumen. The balloon directs the catheter along the flow of blood as the catheter is further advanced from the vena cava through the right atrium, right ventricle and into the main pulmonary artery. The catheter is advanced until the balloon impinges upon the walls of an individual pulmonary artery or capillary. In this position, referred to as the wedged position, the inflated catheter balloon seals off the inflow of blood through the artery or capillary. The hemodynamic pressure may then be measured using a pressure measuring gauge coupled to the proximal port of the second lumen. In addition, a bolus of cold water may be injected through the third lumen into the heart and out of the opening located 30 cm from the distal tip of the catheter. The temperature change caused by thermodilution is then measured downstream at the thermistor and used to calculate the cardiac output in accordance with the well-known Fick principle.

A principle disadvantage of the cardiac monitoring catheters now in use is that it is frequently difficult to reliably obtain a wedge pressure measurement after the catheter has been placed and sewn into position. Once a pressure measurement has been made, the catheter balloon is deflated. The balloon is reinflated for subsequent pressure measurements. Success in obtaining such pressure measurements is dependent upon the distal tip of the catheter remaining in the position of original placement. Migration of the catheter tip out of the original pulmonary artery and into a different pulmonary artery may prevent the balloon from completely occluding the artery. Accordingly, it would not be possible to obtain subsequent pressure measurements. Conversely, the catheter tip may migrate into a permanently wedged position wherein the artery remains occluded even when the balloon has deflated. This condition is likely to cause a pulmonary infarction due to prolonged interruption of pulmonary blood flow and may also cause erosion injury to the pulmonary artery wall.

The present invention overcomes the above-noted disadvantages of catheters presently in use. Migration of the distal tip of the catheter is minimized so that it is generally always possible to obtain a pressure measurement. In addition, the disclosed catheter will never become permanently wedged. These and other advantages of the subject invention will become apparent to a person having ordinary skill in the art upon a reading of the following Best Mode for Carrying out the Invention together with the drawings.

DISCLOSURE OF THE INVENTION

A catheter assembly for measuring hemodynamic pressure and method is disclosed. The assembly is comprised of two catheters including an outer catheter having a first lumen in which is slidably disposed an inner catheter having second and third lumens. An inflatable balloon is positioned at the distal end of the inner catheter, with the interior of the balloon being in communication with the second lumen.

The assembly further includes an inflation port disposed at the proximal end of the inner catheter which is in communication with the second lumen. The inflation port is for coupling to a balloon inflation source such as a gas filled syringe. A pressure port, also located at the proximal end of the inner catheter, is in communication with the third lumen. The pressure port is for coupling to a conventional pressure measurement apparatus.

In operation, the distal section of the subject catheter assembly is inserted in the heart of the patient in the conventional manner, with the inner catheter substantially retracted within the outer catheter. The balloon is inflated through the second lumen so that the catheter assembly tip will be guided by blood flow until the tip of the assembly is positioned in the pulmonary artery bed. The catheter assembly is then advanced until the balloon occludes a pulmonary artery or capillary, i.e. until the balloon is in a wedged position. Once the balloon is in the wedged position, hemodynamic pressure measurements may be made utilizing the third lumen.

Once the pressure measurement has been made, the balloon is deflated, and the assembly is pulled back a small distance, typically approximately 7 cm, so that the distal tip of the inner catheter will remain in the main pulmonary artery. The outer catheter is then stitched in place. Subsequent pressure measurements are made by reinflating the balloon and advancing the inner catheter through the outer catheter until the balloon occludes a pulmonary artery or capillary. A pressure measurement is then made, the balloon is deflated, and the inner catheter is retracted back through the outer catheter.

BRIEF DESCRIPTION OF THE DRAWINGS

FIG. 1 is a perspective view of the subject catheter assembly.

FIG. 2 is a schematic representation of the subject catheter assembly positioned in the heart of a patient with the inner catheter retracted.

FIG. 3 is a schematic representation of the subject catheter assembly positioned in a the heart of a patient with the inner catheter extended to a wedged position.

FIG. 4 is a cross-sectional view of the subject catheter assembly with the inner catheter in a retracted position and the catheter balloon deflated.

FIG. 5 is a cross-sectional view taken through section line 5—5 of FIG. 4 showing a cross-section of the inner and outer catheters.

FIG. 6 is a cross-sectional view of the subject catheter assembly with the inner catheter in an extended position and the catheter balloon inflated.

BEST MODE FOR CARRYING OUT THE INVENTION

Figure 7:
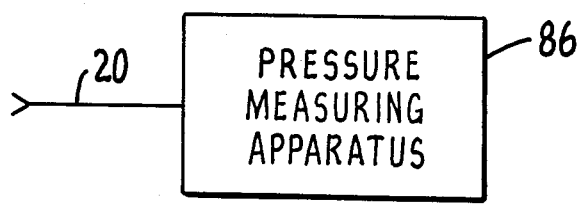
FIG. 7 is a block diagram representing a pressure measuring apparatus for use in measuring hemodynamic pressure.

Referring now to FIGS. 1 and 4 through 5 of the drawings, the subject catheter assembly preferably includes an elongated mounting plate 10. A fixed retaining ring 12 is rigidly secured to one end of plate 10. Ring 12 includes a first opening (not designated) which receives a proximal end of a flexible outer catheter 14 which is typically approximately 110 cm in length. As can best be seen in FIG. 4, retaining ring 12 is provided with a syringe port 44 which is in communication with the lumen 62 of outer catheter 14.

Retaining ring 12 includes a second opening (not designated) which is coaxial with the first opening and which receives the proximal end of catheter 14. The second opening slidably receives one end of a rigid tube 52. An annular recess in the ring extends around the second opening for receiving a resilient sealing ring 54.

The remaining end of rigid tube 52 is securely fitted within a circular bore of a movable retaining ring 16. Ring 16 is provided with a annular recess 42 which receives a resilient locking member 18 secured to plate 10. As will be subsequently described, locking member 18 engages the recess 42 of the locking member thereby securing the movable retaining ring in what can be termed an extended position.

The subject assembly further includes a flexible inner catheter 26 which is disposed within the lumen 62 of outer catheter 14 and which is approximately 10 cm longer than the outer catheter.

Thus, it can be seen that the outer catheter extends along a substantial length of the inner catheter. As can best be seen in FIG. 5, the outer diameter of inner catheter 26 is approximately one-half the inner diameter of catheter 14. Inner catheter 26 has an interior arcuate partition which divides the interior of the catheter into separate lumens 56 and 58. As will be explained later in greater detail, lumen 56 conducts the gas for inflating the catheter balloon and lumen 58 is used for cardiac pressure measurements. Lumen 62 of outer catheter 14 is sufficiently large to accommodate inner catheter 26 and further serves to transmit a frigid solution used for measuring cardiac output by way of thermodilution.

The proximal end of inner catheter 14 is positioned securely within rigid tube 52. Openings are formed in the relatively rigid tube and inner catheter 26 which are coincident with syringe port 46 so that the port will be in communication with lumen 56 of the inner catheter. In addition, movable retaining ring 16 includes a port 48 formed in the end of the ring which is in communication with lumen 58 of the inner catheter. Port 48 receives the input 20 (FIG. 1) of a conventional pressure measuring apparatus as represented by block 86 depicted in FIG. 7.

A collapsible sleeve 28 is positioned between fixed retaining ring 12 and movable retaining ring 16. Each of the retaining rings is provided with an annular section for receiving the end of the sleeve. A seal is effected between the sleeve and the rings by securing bands 50.

A conventional thermistor 30 is secured to the outer wall of outer catheter 14, approximately 5 cm from the distal tip of the catheter. The termistor leads extend through lumen 62 of the outer catheter to fixed retaining ring 12. The leads 32 exit through an opening (not designated) in the ring and are for coupling to conventional temperature measuring apparatus. A seal (not depicted) extends around the retaining ring lead opening to prevent the escape of thermodilution fluid.

A thermodilution outlet 38 is located in an outer catheter 14 approximately 35 cm from the distal tip of the catheter. Frigid solution present in lumen 62 is dispensed out of outlet 38. A seal 36 is positioned at the distal end of outer catheter 14 which seals lumen 62 while permitting relative movement between the inner and outer catheters. A catheter balloon 34 in the form of a sleeve of elastomer material is positioned over the distal end of inner catheter 26. Securing bands 68 are wound around each end of the balloon so as to form an airtight seal between the balloon and the inner catheter. A balloon inflation opening 66 is formed in the inner catheter well approximately midway between band 68 so as to couple the interior of the balloon with lumen 56. A plug 64 is positioned within lumen 56 at the distal end of the inner catheter 26 thereby sealing the lumen.

Figure 8:
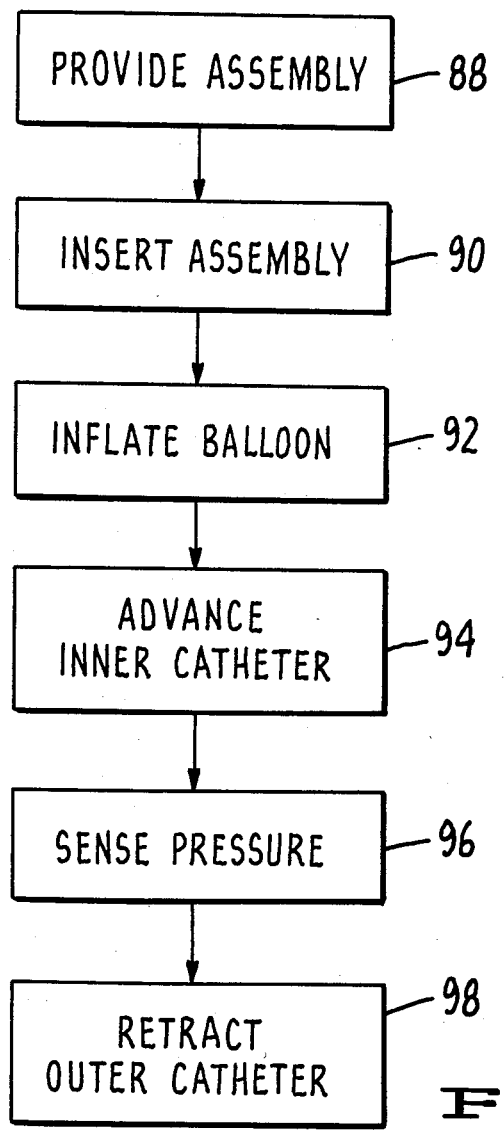
FIG. 8 is a simplified flow chart illustrating the disclosed method of measuring hemodynamic pressure.

Having described the construction of the subject catheter assembly, operation of the assembly will now be given. First, a gas filled syringe 22 (FIG. 1) is inserted within the inflation syringe port 46 of movable retaining ring 16. In addition, a frigid solution injecting ring 24 is positioned within thermodilution syringe port 44 of fixed retaining ring 12. Movable retaining ring 16 is then set in the retracted position using locking member 18. In this position, inner catheter 26 is retracted within outer catheter 14. The assembly as thus provided and prepared is depicted by step 88 in the chart of FIG. 8. The locking member serves as a guide by indicating that the inner catheter is in a fully retracted position.

The tip of the catheter assembly is then introduced into a central vein and advanced towards the right heart in the same manner as a conventional catheter assembly. This introduction is depicted by step 90 in FIG. 8. Once the distal tip is positioned in the vena cava, balloon 34 is inflated, as depicted by step 92 in FIG. 8, through lumen 56 utilizing inflation syringe 22. Preferably, the balloon is inflated to a diameter of approximately 1.3 mm by injecting approximately 1.5 cc of air. Balloon 34 guides the distal portion of the catheter assembly along the flow of blood through the right atrium, right ventricle and into the pulmonary artery 74 (FIG. 2) and through the pulmonary valve 76. The catheter continues to be advanced, as depicted by step 94 in FIG. 8, until a pulmonary artery 78 is occluded. A pressure measurement then can be made by sensing hemodynamic pressure through lumen 58 in the conventional manner, as depicted by step 96 in FIG. 8. Balloon 34 is then deflated and the entire catheter assembly is retracted approximately 7 cm, as depicted by step 98 in FIG. 8 and illustrated in FIG. 2, and sewn into position. At this time, capacity measurements can be made in the conventional manner by injecting a frigid solution, using syringe 24, into the heart through outlet 38 and measuring the rate of temperature change by monitoring the output of thermistor 30 on leads 32.

When the catheter assembly is in the retracted position, the distal tip of the catheter will remain in the main pulmonary artery 74. When further pressure measurements are to be made, the physician first verifies that the distal tip of the catheter is still positioned in the main pulmonary artery by monitoring the pressure via lumen 58. Balloon 34 can then be reinflated and the catheter assembly placed in an extended position by sliding movable retaining ring 16 towards the fixed ring as shown in phantom in FIG. 1. As can best be seen in FIG. 6, rigid tube 52 is forced through seal 54 guiding the inner catheter 26 and causing the catheter to translate within lumen 62 of outer catheter 14. The inner catheter is advanced until it is in a wedged position as depicted in FIG. 3. The original artery 78 or another pulmonary artery, such as artery 80, may be occluded. In either event, a pressure measurement may then be made. The capability of effectively adjusting the length of the catheter assembly ensures that a wedged position can be obtained in any pulmonary artery cannulated.

Syringe 24 is also used for flushing lumen 62 prior to insertion of the catheter. Flexible sleeve 28 ensures that the translating inner catheter 26 remains sterile and seal 54 prevents fluids injected through port 44 from backing into the interior of the sleeve. Locking member 18 not only secures the movable retaining ring 16 in place, but serves to guide the physician so that the inner catheter 26 is not retracted to such an extent that balloon 34 strikes the distal end of outer catheter 14. Sleeve 28 inherently serves as retaining means to prevent the inner catheter 26 from being inadvertently fully retracted from the outer catheter 14 so that the two catheters remain inseparable. A similar function is provided by balloon 34 in combination with seal 36 as can be seen in FIG. 4.

Thus, a novel catheter assembly having an outer catheter and a translatable inner catheter has been disclosed. Although a preferred embodiment of the subject catheter assembly has been described in some detail, it is to be understood that changes can be made by persons skilled in the art without departing from the spirit and scope of the subject invention as defined by the appended claims.

I claim:

1. A catheter assembly comprising:
   an outer catheter having a first lumen;
   an inner catheter slidably disposed in said first lumen of said outer catheter and having second and third lumens, with said outer catheter extending along a substantial length of said inner catheter;
   retaining means to prevent said inner catheter from being fully retracted from said outer catheter;
   an inflatable balloon disposed at a distal end of said inner catheter, with the said balloon having an interior which is in communication with said second lumen;
   an inflation port disposed at a proximal end of said inner catheter, opposite said distal end, and in communication with said second lumen, said inflation port for coupling to a balloon inflation source; and
   a pressure port disposed at said proximal end of said inner catheter and in communication with said third lumen, said pressure port for coupling to pressure measurement apparatus.

2. The catheter assembly of claim 1 further comprising a thermodilution port located at a proximal end of said outer catheter and in communication with said first lumen, said thermodilution port for coupling to a source of thermodilution solution and wherein said outer catheter is provided with a thermodilution outlet in communication with said first lumen near a distal end of said outer catheter, opposite said proximal end.

3. The catheter assembly of claim 2 further comprising temperature measuring means for measuring temperature which is disposed between said distal end of said outer catheter and said thermodilution outlet.

4. The catheter assembly of claim 3 wherein said temperature measuring means includes a thermistor.

5. The catheter assembly of claim 4 further comprising thermistor leads coupled to said thermistor which extend through said first lumen towards said proximal end of said outer catheter.

6. The catheter assembly of claim 1 further comprising a mounting plate and fixed retaining means for rigidly securing said proximal end of said outer catheter to said mounting plate.

7. The catheter assembly of claim 6 wherein said fixed retaining means is a fixed retaining ring having a central opening which receives said inner catheter.

8. The catheter assembly of claim 7 further comprising movable retaining means for guiding said inner catheter through said central opening of said fixed retaining ring.

9. The catheter assembly of claim 8 wherein said movable retaining means comprises a relatively rigid tube which receives said proximal end of said inner catheter and is slidably disposed in said central opening of said fixed retaining ring.

10. The catheter assembly of claim 9 wherein said movable retaining means further comprises a moveable retaining ring secured to said rigid tube.

11. The catheter assembly of claim 10 wherein said inflation port is formed in said movable retaining ring.

12. The catheter assembly of claim 11 wherein said pressure port is formed in said movable retaining ring.

13. The catheter assembly of claim 12 further comprising locking means for detachably securing said movable retaining ring to said plate.

14. The catheter assembly of claim 13 further comprising a collapsible sleeve coupled between said fixed and said movable retaining rings.

15. The catheter assembly of claim 7 further comprising a thermodilution port formed in said fixed retaining ring and in communication with said first lumen, said thermodilution port for coupling to a source of thermodilution solution and wherein said outer catheter is provided with a thermodilution outlet opening in communication with said first lumen near a distal end of said outer catheter.

16. The catheter assembly of claim 15 wherein said fixed retaining ring has a central opening and wherein said assembly further comprises movable retaining means for guiding said inner catheter through said central opening with said movable retaining means including a relatively rigid tube which receives said proximal end of said inner catheter and is slidably disposed in said central opening.

17. The catheter assembly of claim 1 wherein said retaining means includes a collapsible sleeve disposed around said inner catheter with a first end of said sleeve secured to a proximal end of said outer catheter, opposite said distal end, and a second end of said sleeve secured to said proximal end of said inner catheter.

18. A method of measuring pulmonary artery and pulmonary capillary hemodynamic pressure comprising the following steps:
   providing a catheter assembly which includes an outer catheter having a first lumen and an inner catheter slidably disposed in said first lumen, said inner catheter having second and third lumens and an inflatable balloon disposed at a distal end thereof and inflatable through said second lumen;

inserting a distal section of said catheter assembly, including at least a portion of said outer catheter, into the heart of a patient;

inflating said balloon through said second lumen;

advancing said inner catheter through said outer catheter until said balloon occludes a pulmonary artery or capillary;

sensing hemodynamic pressure through said third lumen; and retracting said inner catheter through said outer catheter.

19. The method of claim 18 wherein, subsequent to said inserting step, the following additional steps are included for positioning said outer catheter:

inflating said balloon through said second lumen;

advancing said inner and outer catheters together until said balloon occludes a pulmonary artery or capillary;

retracting said inner and outer catheters;

securing a proximal end of said outer catheter to restrict movement of said proximal end with respect to the patient; and deflating said balloon.

* * * * *